US008527251B2

(12) United States Patent
Ionasec et al.

(10) Patent No.: US 8,527,251 B2
(45) Date of Patent: Sep. 3, 2013

(54) METHOD AND SYSTEM FOR MULTI-COMPONENT HEART AND AORTA MODELING FOR DECISION SUPPORT IN CARDIAC DISEASE

(75) Inventors: Razvan Ioan Ionasec, Lawrenceville, NJ (US); Puneet Sharma, Rahway, NJ (US); Bogdan Georgescu, Plainsboro, NJ (US); Andrey Torzhkov, Jersey City, NJ (US); Fabian Moerchen, Rocky Hill, NJ (US); Gayle M. Wittenberg, Plainsboro, NJ (US); Dmitriy Fradkin, Princeton, NJ (US); Dorin Comaniciu, Princeton Junction, NJ (US)

(73) Assignee: Siemens Aktiengesellschaft, Munich (DE)

( * ) Notice: Subject to any disclaimer, the term of this patent is extended or adjusted under 35 U.S.C. 154(b) by 768 days.

(21) Appl. No.: 12/770,850

(22) Filed: Apr. 30, 2010

(65) Prior Publication Data
US 2010/0280352 A1 Nov. 4, 2010

Related U.S. Application Data

(60) Provisional application No. 61/174,588, filed on May 1, 2009.

(51) Int. Cl.
*G06G 7/58* (2006.01)
(52) U.S. Cl.
USPC ................................................ 703/11
(58) Field of Classification Search
USPC ............... 703/2, 11; 707/104.1; 600/1, 466, 600/438, 523; 382/131; 434/262
See application file for complete search history.

(56) References Cited

U.S. PATENT DOCUMENTS

| 7,117,026 | B2 | 10/2006 | Shao et al. |
| 7,450,780 | B2 | 11/2008 | Roche et al. |
| 2006/0004274 | A1 | 1/2006 | Hawman |
| 2006/0004275 | A1 | 1/2006 | Vija et al. |
| 2007/0130206 | A1* | 6/2007 | Zhou et al. ............. 707/104.1 |
| 2007/0135803 | A1* | 6/2007 | Belson ...................... 606/1 |
| 2008/0077032 | A1* | 3/2008 | Holmes et al. ........... 600/523 |
| 2008/0101676 | A1 | 5/2008 | Zheng et al. |
| 2008/0262814 | A1 | 10/2008 | Zheng et al. |

(Continued)

OTHER PUBLICATIONS

Taylor et al., "Experimental and computational methods in cardiovascular fluid mechanics", Annual Review of fluid mechanics, 2004.*

(Continued)

*Primary Examiner* — Kandasamy Thangavelu

(57) ABSTRACT

A method and system for generating a patient specific anatomical heart model is disclosed. Volumetric image data, such as computed tomography (CT), echocardiography, or magnetic resonance (MR) image data of a patient's cardiac region is received. Individual models for multiple heart components, such as the left ventricle (LV) endocardium, LV epicardium, right ventricle (RV), left atrium (LA), right atrium (RA), mitral valve, aortic valve, aorta, and pulmonary trunk, are estimated in said volumetric cardiac image data. A multi-component patient specific anatomical heart model is generated by integrating the individual models for each of the heart components. Fluid Structure Interaction (FSI) simulations are performed on the patient specific anatomical model, and patient specific clinical parameters are extracted based on the patient specific heart model and the FSI simulations. Disease progression modeling and risk stratification are performed based on the patient specific clinical parameters.

20 Claims, 10 Drawing Sheets

(56) References Cited

U.S. PATENT DOCUMENTS

| | | | |
|---|---|---|---|
| 2008/0287803 A1* | 11/2008 | Li et al. | 600/466 |
| 2009/0123050 A1 | 5/2009 | Ionasec et al. | |
| 2009/0130643 A1* | 5/2009 | Cusano | 434/262 |
| 2009/0149751 A1* | 6/2009 | Mourad et al. | 600/438 |
| 2010/0017171 A1* | 1/2010 | Spilker et al. | 703/2 |
| 2010/0070249 A1 | 3/2010 | Ionasec et al. | |
| 2010/0278405 A1* | 11/2010 | Kakadiaris et al. | 382/131 |

OTHER PUBLICATIONS

Sermesant et al., "Deformable biomechanical models: application to cardiac image analysis", Medical image analysis, 2003.*

Sermesant et al., "Cardiac function estimation from MRI using a heart model and data assimilation: advances and difficulties", Medical image analysis, 2006.*

Burton et al., "Three dimensional models of individual cardiac histoanatomy: Tools and challenges", Annals of the Newyprk Academy of Sciences, 2006.*

Ionasec, Razvan Ioan et al., "Dynamic Model-Driven Quantitative and Visual Evaluation of the Aortic Valve from 4D CT", Int'l Conference on Medical Image Computing and Computer-Assisted Intervention, 11(Pt 1), 2008.

Yang, Lin et al., "3D UltraSound Tracking of the Left Ventricles Using One-Step Forward Prediction and Data Fusion of Collaborative Trackers", CVPR, 2008.

Zheng, Yefeng, et al., "Four-Chamber Heart Modeling and Automatic Segmentation for 3D Cardiac CT Volumes Using Marginal Space Learning and Steerable Features", IEEE Transactions on Medical Imaging, 27(11), Nov. 2008.

* cited by examiner

US 8,527,251 B2

METHOD AND SYSTEM FOR MULTI-COMPONENT HEART AND AORTA MODELING FOR DECISION SUPPORT IN CARDIAC DISEASE

This application claims the benefit of U.S. Provisional Application No. 61/174,588, filed May 1, 2009, the disclosure of which is herein incorporated by reference.

BACKGROUND OF THE INVENTION

The present invention relates to modeling the heart in medical images, and more particularly, to using personalized 4D anatomical heart model of the full cardiac system estimated from volumetric image sequences for decision support in diagnosis and treatment of cardiac disease.

Cardiac disease is the leading cause of death for men and women in the United States and accounts no less than 30% of deaths worldwide. Although medical advances in recent years have provided important improvements in the diagnosis and treatment of complex cardiac diseases such as valvular disease, thoracic aortic aneurysm, and Tetralogy of Fallot, the incidence of premature morbidity and mortality is still large. Medical imaging modalities, such as computed tomography (CT), magnetic resonance (MR), rotational X-ray, and Ultrasound, can be used to acquire large amounts of morphological and functional image data with a high temporal-spatial resolution. However, due to a lag in data understanding capabilities, physicians are forced to make vital decisions based on measurements and methods that are limited in scope. Thus, for many cardiac diseases, there is currently no prognostic model that allows comprehensive decision-making regarding optimal patient assessment, surgical intervention, or the extent of the cardiac disease. These limitations are at least in part due to the lack of efficient and accurate estimation of patient-specific parameters describing the heart-aortic anatomy, physiology, and hemodynamics, as well as the lack of disease progression models.

BRIEF SUMMARY OF THE INVENTION

The present invention provides a method and system for decision support in treatment and prognosis of cardiac disease using a personalized anatomic model of the heart generated from volumetric image data.

In one embodiment of the present invention, a multi-component patient specific 4D geometric model of the heart and aorta is estimated from a sequence of volumetric cardiac imaging data. A patient specific 4D computational model is generated based on one or more of personalized geometry, material properties, fluid boundary conditions, and flow velocity measurements in the 4D geometric model. A patient specific biomechanical model is generated based on Fluid Structure Interaction (FSI) simulations using the 4D computational model. Patient specific clinical parameters are extracted based on the 4D geometric model and the FSI simulations. Disease progression modeling and risk stratification are performed based on the patient specific clinical parameters.

These and other advantages of the invention will be apparent to those of ordinary skill in the art by reference to the following detailed description and the accompanying drawings.

DETAILED DESCRIPTION

The present invention relates to generating a 4D personalized anatomical model of the heart from a sequence of volumetric data, such as computed tomography (CT), magnetic resonance imaging (MRI), and echocardiography data. Such sequences of volumetric data also referred to herein as 4D image data or 4D images, are sequences taken over a period of time to cover one or more cardiac cycles, in which each frame is a 3D image (volume). Embodiments of the present invention are described herein to give a visual understanding of the heart modeling method. A digital image is often composed of digital representations of one or more objects (or shapes). The digital representation of an object is often described herein in terms of identifying and manipulating the objects. Such manipulations are virtual manipulations accomplished in the memory or other circuitry/hardware of a computer system. Accordingly, is to be understood that embodiments of the present invention may be performed within a computer system using data stored within the computer system.

Embodiments of the present invention are directed to generating a comprehensive and personalized computational model of the full heart and aorta from high resolution CT, MR, and rotational X-ray imaging, in order to guide decision support for patient evaluation, risk stratification, procedure planning, and timing of surgical intervention. Subtle, but critical interconnections are estimated between the aorta and the heart's components and disease progression models are derived. Embodiments of the present invention include the following components: 1) patient-specific models of the aorta, aortic valve, mitral valve, and left and right ventricles and atria; 2) simulations for Fluid Structure Interaction (FSI); 3) advanced clinical parameters derived from the heart models; and 4) disease progression models for cardiac disease to predict the risk of specific conditions.

As described herein, complete personalized modeling of the heart chambers, valves, and aorta using advanced computational techniques in conjunction with rich imaging (e.g., CT, MR, Rotational X-ray) allows discovery and testing of practical decision support algorithms for improved management of cardiac disease. Successful personalized modeling of cardiac disease provides practical support for the complex surgical decision process with the goal of decreasing morbidity and mortality. The identification of risk models allows appropriate timing of surgical intervention, validates the efficacy of current medical therapy, and provides insight into the design of new therapies.

Figure 1:
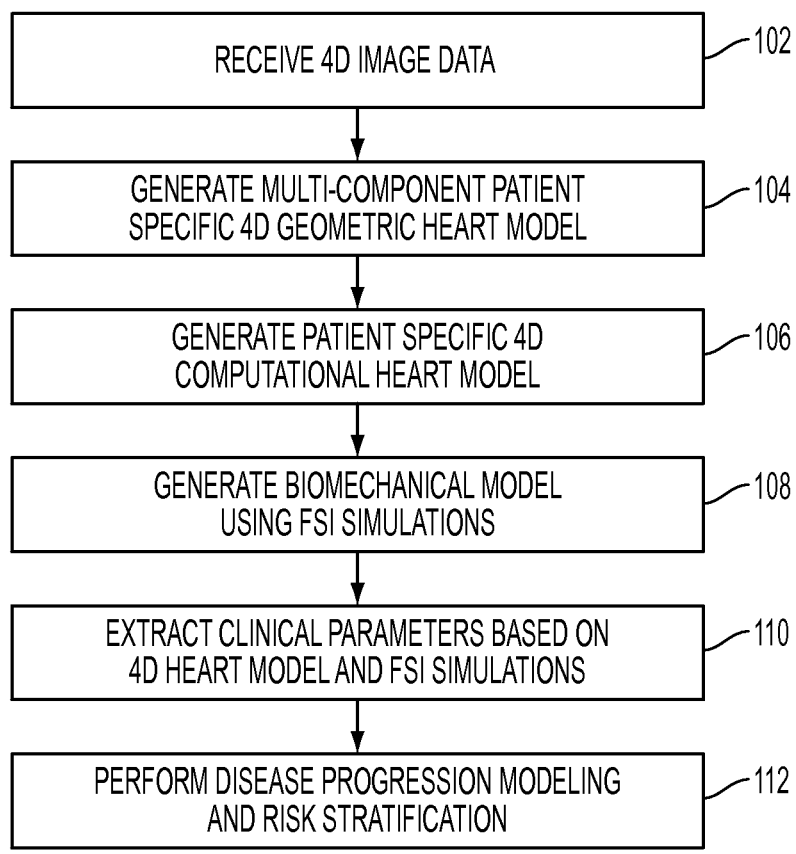
FIG. 1 illustrates a method for multi-component heart and aorta modeling and cardiac disease decision support according to an embodiment of the present invention.
Figure 2:
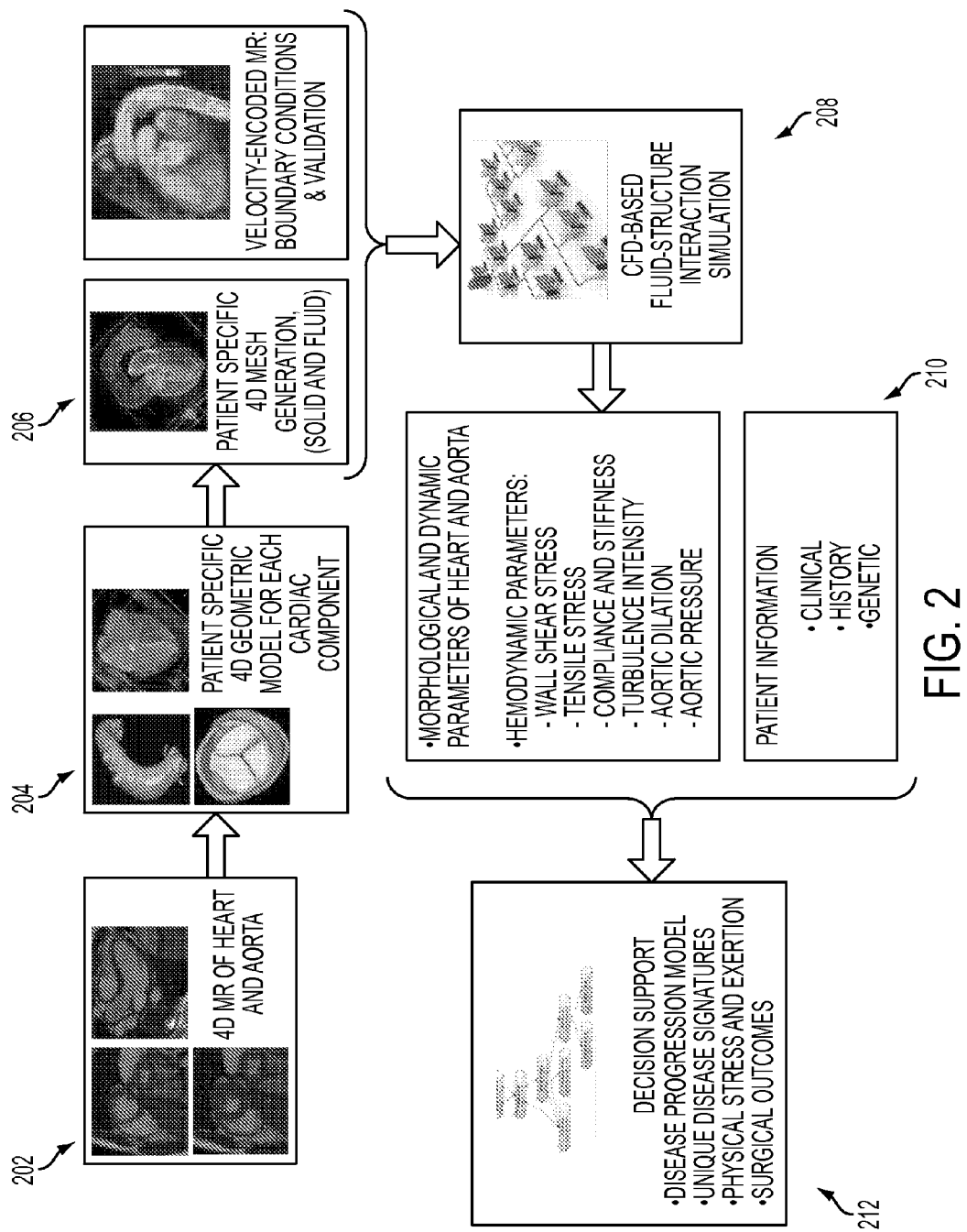
FIG. 2 illustrates an example of the multi-component hear and aorta modeling and decision support method of FIG. 1 according to an embodiment of the present invention.

FIG. 1 illustrates a method for multi-component heart and aorta modeling and cardiac disease decision support according to an embodiment of the present invention. The method of FIG. 1 transforms image data representing a coronary region of a patient into an anatomical model of the heart and uses the heart model for decision support in diagnosing and treating cardiac disease. FIG. 2 illustrates an example of the multi-component heart and aorta modeling and decision support method of FIG. 1 according to an embodiment of the present invention.

Referring to FIG. 1, at step 102, 4D image data is received. In particular, at least one sequence of volumetric image data is received. The sequence of volumetric image data can be a sequence of 3D images (volumes) acquired over a certain time period. For example, such a 4D image data (3D+time) can be acquired over a one full heart cycle. One or more sequences can be received using various medical imaging modalities. For example, according to various embodiments of the present invention, 4D CT data, 4D echocardiography, and 4D magnetic resonance (MR) image data can be received, as well as other types of image data. The image data can be received directly from one or more image acquisition devices, such as a CT scanner, an ultrasound device, or an MR scanner. It is also possible that previously stored image data be loaded, for example from a memory or storage of a computer system or some other computer readable storage medium. As illustrated in FIG. 2, 4D MR data is received at step 202.

Returning to FIG. 1, at step 104, a multi-component patient-specific 4D geometric model is estimated from the received 4D image data. In particular, a 4D geometric model is generated from the received image data for each of multiple cardiac components, such as the aorta, aortic valve, mitral valve, tricuspid valve, pulmonary valve, and left and right ventricles and atria. As illustrated in FIG. 2, at step 204, patient specific 4D geometric heart models are generated for each cardiac component.

Figure 3A:
FIGS. 3A-3D illustrate exemplary patient-specific models generated for cardiac components from received image data.
Figure 3B:
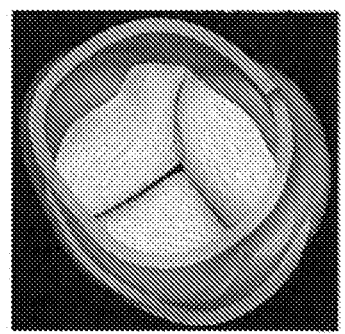
Figure 3C:
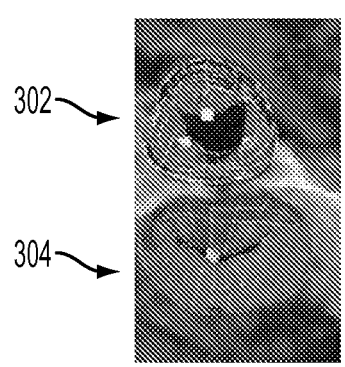
Figure 3D:
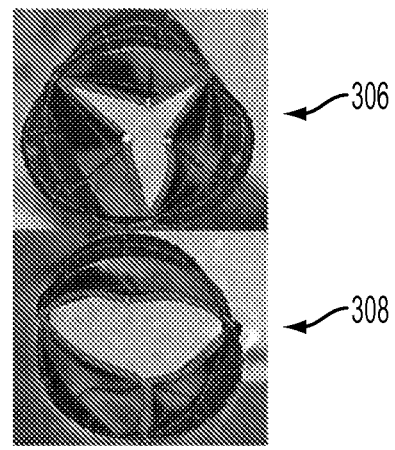

FIGS. 3A-3D illustrate exemplary patient-specific models generated for cardiac components from received image data. FIG. 3A shows a patient-specific model of the aorta and the ostia derived from CT data. FIG. 3B shows a patient specific model of the aortic valve generated from transesophageal echocardiogram (TEE) data. FIG. 3C shows a patient specific model of coupled aortic (302) and mitral (304) valves generated from TEE data. FIG. 3D shows a patient specific model of pathological aortic valves. In particular, FIG. 3D shows a stenotic aortic valve 306 and a bicuspid aortic valve 308.

Figure 4:
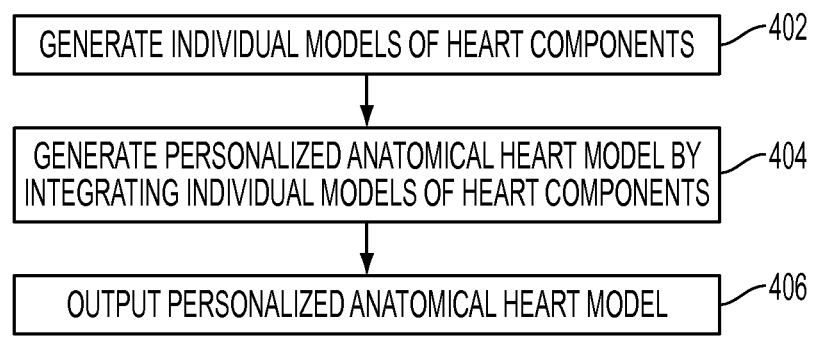
FIG. 4 illustrates a method for generating a 4D personalized geometric model of the heart according to an embodiment of the present invention.

The multi-component 4D geometric model gives the morphology of the patient's heart and can be used to determine morphological (dimensions) and dynamic parameters for any component of the heart. For example, the patient specific 4D geometric model can be used to measure the left ventricle (LV) volume and ejection fraction (EF), inter-chamber synchronicity analysis, aortic and mitral valve analysis, etc. FIG. 4 illustrates a method for generating a 4D personalized geometric model of the heart according to an embodiment of the present invention. The method of FIG. 4 transforms image data representing a coronary region of a patient to generate a personalized geometric model of the heart for that patient. The method of FIG. 4 can be used to implement step 104 of the method of FIG. 2.

At step 402, an individual model is generated from the received image data for each of a plurality of heart components. According to an embodiment of the present invention, models are generated for the heart chambers: left ventricle (LV) (endocardium and epicardium), right ventricle (RV), left atrium (LA) and right atrium (RA); valves: mitral valve and aortic valve; and main vessels: aorta and pulmonary trunk. All of these portions of the heart are referred to herein collectively as the "heart components". For each heart component, a physiological model of the heart component is estimated in each frame of the 4D image data using a discriminative database-guide estimation/detection technique.

The physiological model of each anatomic structure (heart component) is constructed offline prior to generating the personalized heart model for a particular patient. Each physiological model is generated based on a mathematical representation of the corresponding heart component in a set of annotated training data. For example, the physiological model for each heart component can be generated using mean shapes of the heart component in a set of annotated training data. For example, United States Patent Application Publication No. 2008/0101676, which is incorporated herein by reference, describes a generating a four-chamber physiological heart model and fitting the heart model to image data. As described therein, the heart model is a 3D mesh and initial meshes for each chamber are generated using mean shapes of the chambers in annotated training data. Further, United States Patent Application No. 2009/0123050, which is incorporated herein by reference, describes a 4D physiological model of the aortic valve. A physiological model can similarly be generated offline for each of the heart components based on a set of annotated training data.

In order to estimate a physiological model of a particular heart component in a 3D image (i.e., frame of a 4D image sequence), the parameters of the physiological model are estimated to fit the image using a discriminative machine-learning technique based on a large database of annotated training images. According to one embodiment, marginal space learning (MSL) is used to localize the physiological model in each of the images.

The idea of MSL is not to learn a classifier directly in a full similarity transformation parameter space, but to incrementally learn discriminative classifiers in increasing dimensionality based on annotated training data. As the dimensionality increases, the valid (positive) space region becomes more restricted by previous marginal space classifiers. In order to estimate a physiological model of an anatomic structure, such as a particular heart component, in an image, the estimation of the similarity transformation (i.e., position, orientation, and scale) corresponding to the location of the heart component can be split into three stages: position estimation, position-orientation estimation, and full similarity transformation estimation. A discriminative classifier is trained for each stage based on the training data. All of the discriminative classifiers can be trained as Probabilistic Boosting Trees (PBTs). In addition to reducing the size of the search space, another advantage of MSL is that it is possible to use different features, such as 3D Haar features or steerable features to train the classifier in each marginal space level.

Examples of estimating physiological models of various heart components in 3D image data using MSL are described in the following publications, the disclosures of which are incorporated herein by reference: United States Patent Application Publication No. 2008/0101676, describes estimating a model for each chamber of the in 3D CT image data; United States Patent Application No. 2009/0123050, describes fitting a physiological model of the aortic valve to 4D CT data; and Yang et al., "3D Ultrasound Tracking of the Left Ventricles Using One-Step Forward Prediction and Data Fusion of Collaborative Trackers", CVPR 2008, describes fitting a model of the left ventricle to a sequence of 3D ultrasound images. It is to be understood that each of the heart components can be estimated by fitting a physiological model of the heart component to image data using discriminative machine-learning techniques, similarly to the above examples.

Once the parameters of each individual heart component model are estimated in each frame of the 4D image data, e.g., using MSL, learning-based boundary detection can be performed on the individual heart component model in each image to refine the estimated model parameters. In particular, the boundary of each estimated model can be refined using the learning-based boundary detection to increase the accuracy of the physiological model estimation for each heart component.

Figure 5:
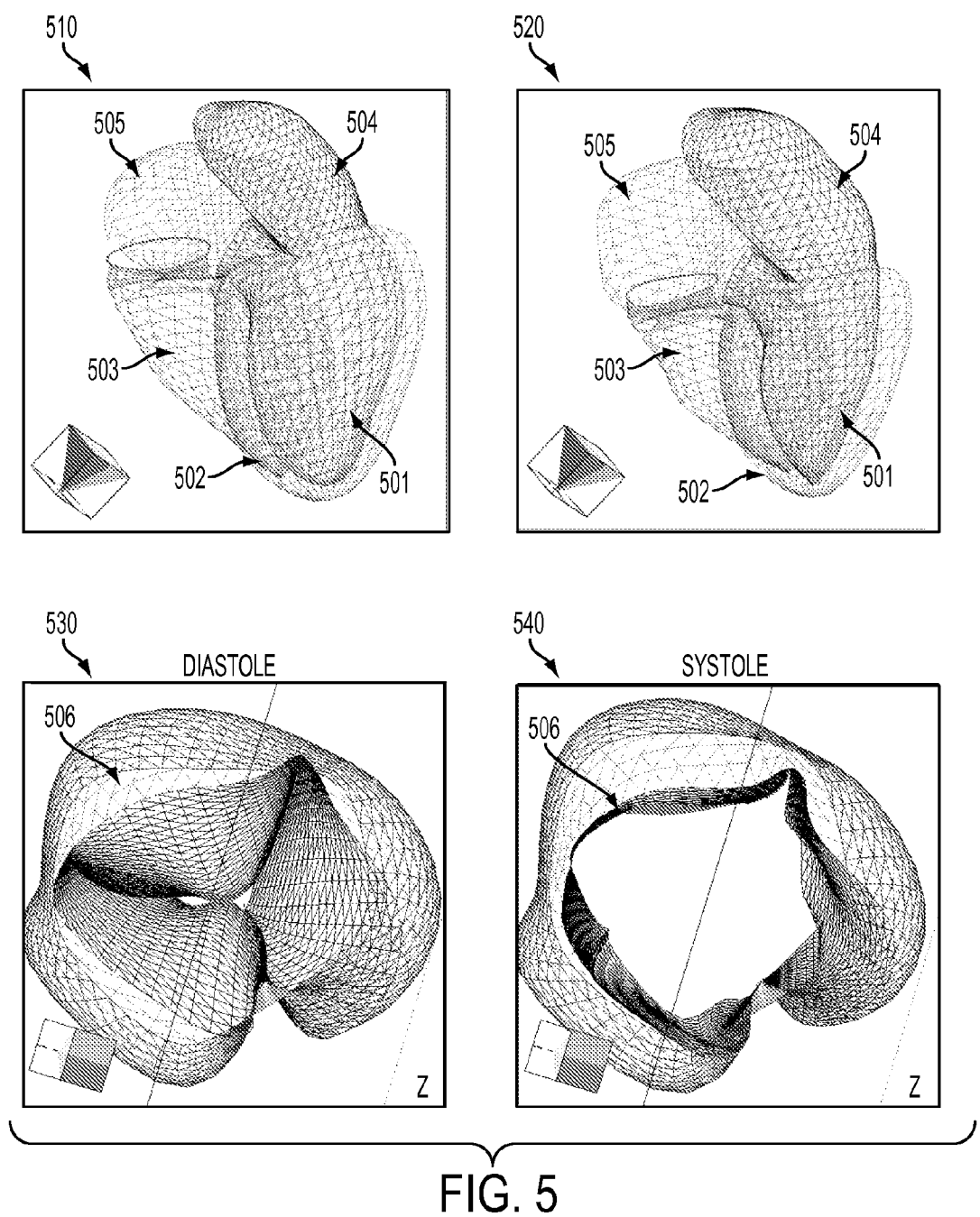
FIG. 5 illustrates exemplary models of the heart chambers and the aortic valve.

FIG. 5 illustrates exemplary models of the heart chambers and the aortic valve. As illustrated in FIG. 5 image 510 shows the LV endocardium 501, the LV epicardium 502, the RV 503, the LA 504, and the RA 505 in diastole and image 520 shows the LV endocardium 501, the LV epicardium 502, the RV 503, the LA 504, and the RA 505 in systole. Image 530 shows the aortic valve 506 in diastole and image 540 shows the aortic valve 506 in systole.

Returning to FIG. 4, at step 404, a 4D personalized anatomical model of the heart is generated by integrating the individual models generated for each of the heart components. Each of the individual heart component models resulting from step 402 is a mesh made of a certain number of points. According to an advantageous implementation, in order to integrate the individual models of the LV (endocardium and epicardium), RV, LA, RA, mitral valve, aortic valve, aorta, and pulmonary trunk, mesh point correspondences are established between connecting or overlapping models. The mesh point correspondences allow the models to be correctly aligned with respect to each other. It is possible to establish mesh point correspondence between models by re-sampling the models. For example, United States Patent Application Publication No. 2008/0262814, which is incorporated herein by reference, describes various re-sampling methods to establish mesh point correspondence between models of the four heart chambers in order to correctly align the heart chamber models. It is to be understood that the techniques described in United States Patent Application Publication No. 2008/0262814 can be extended to establish mesh point correspondence between the individual heart component models described herein.

Figure 6A:
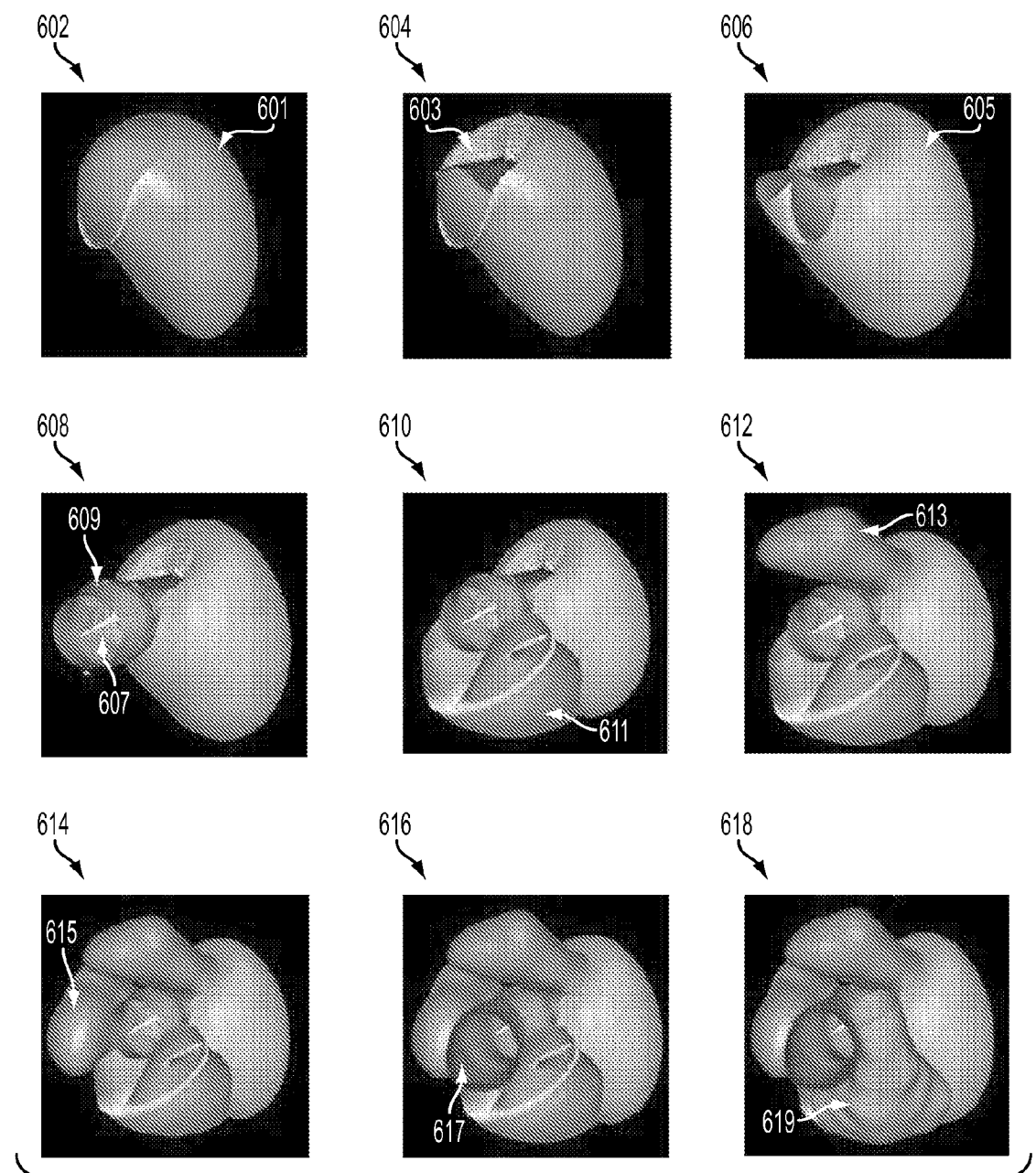
FIGS. 6A and 6B illustrate integrating individual models to generate a personalized anatomical heart model.
Figure 6B:
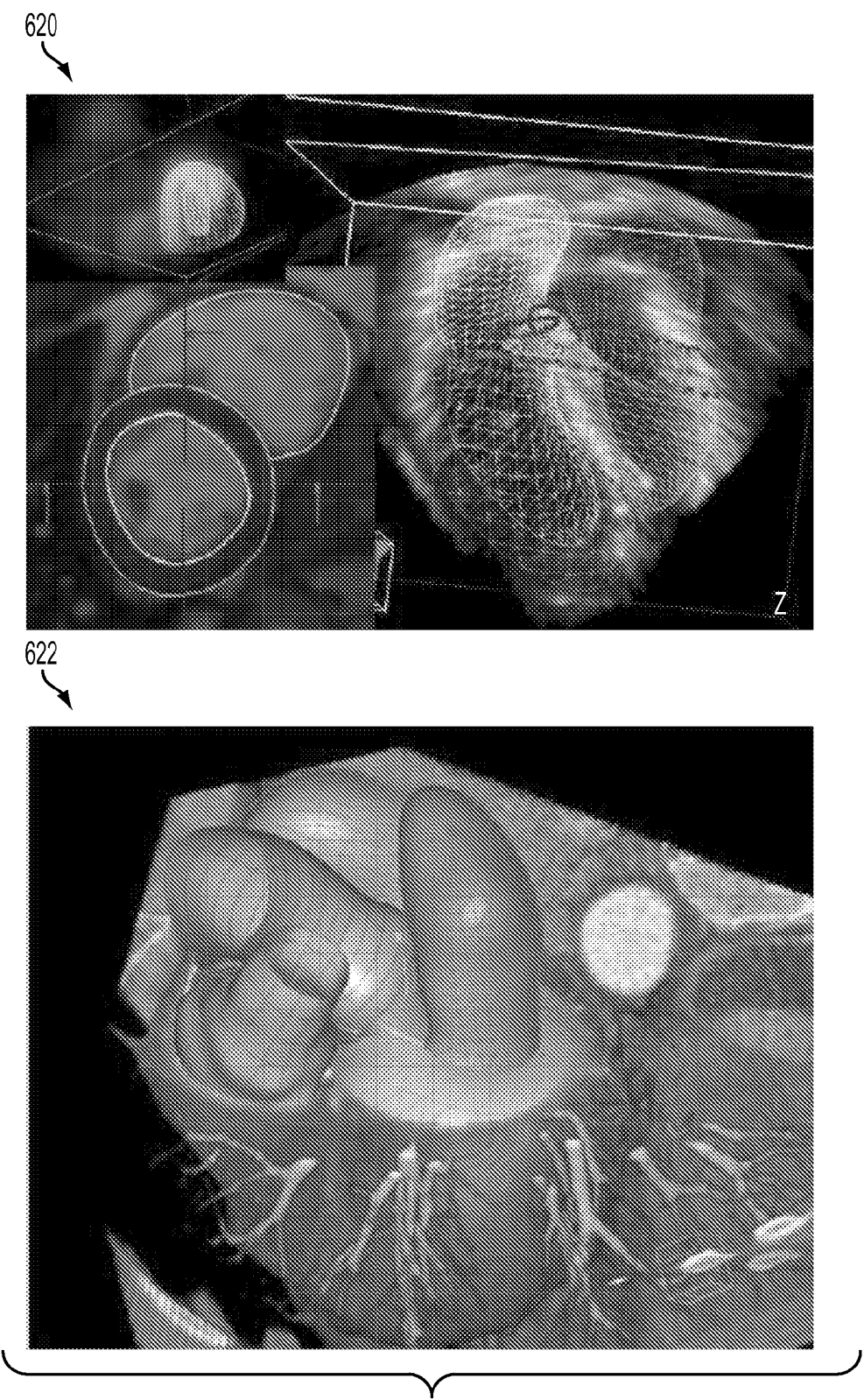

FIGS. 6A and 6B illustrate integrating individual models to generate a personalized anatomical heart model. The images of FIG. 6A illustrate a possible order for integrating the heart component models according to an embodiment of the present invention. As illustrated in FIG. 6A, image 602 shows an LV endocardium model 601. Image 604 shows the integration of the mitral valve model 603. Image 606 shows the integration of the LV epicardium model 605. Image 608 shows the integration of the aortic valve model 607 and the aortic root model 609. Image 610 shows the integration of the RV model 611. Image 612 shows the integration of the LA model 613. Image 614 shows the integration of the RA model 615. Image 616 shows the integration of the aorta model 617. Image 618 shows the integration of the pulmonary trunk model 619. As illustrated in FIG. 6B, images 620 and 622 show 3D renderings of the resulting personalized anatomical heart model fit to image data. It is to be understood that although FIGS. 6A and 6B, illustrate the integration of the heart component models for a 3D volume, the heart component models can be similarly integrated in each frame of a 4D image sequence.

Figure 7A:
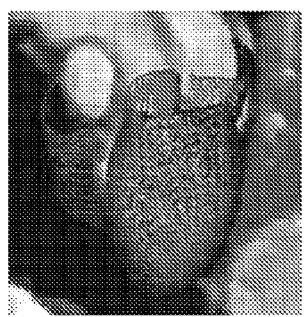
FIGS. 7A-7C illustrate exemplary results of a multi-component, patient specific heart model.
Figure 7B:
Figure 7C:
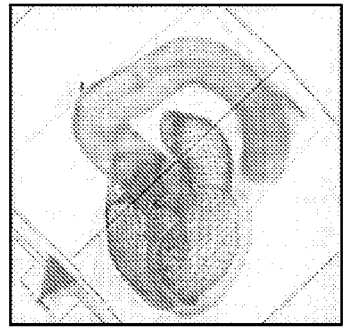

Returning to FIG. 4, at step 406, the 4D personalized anatomical heart model is output. The 4D personalized anatomical heart model can be output by storing the 4D personalized anatomical heart model to a memory, storage, or computer readable medium. The 4D personalized anatomical heart model can also be output by displaying the 4D personalized anatomical heart model or printing an image of the 4D personalized anatomical heart model. The output 4D personalized anatomical heart model can be used for further medical image processing. For example, the 4D personalized anatomical heart model can be used to estimate various morphological and functional measurements, of the heart. The 4D personalized anatomic heart model can also be used to simulate blood flow or blood-tissue interaction. FIGS. 7A-7C illustrate exemplary results of a multi-component, patient specific heart model. FIG. 7A shows left and right ventricles and the aortic root derived from MR data. FIG. 7B shows the left endocardium and epicardium, right ventricle, left and right atria, and the aortic root derived from CT data. FIG. 7C shows all of the above components plus the aorta derived from CT data.

Returning to FIG. 1, at step 106, a patient-specific 4D computational model based on personalized geometry, material properties, fluid boundary conditions, and flow velocity measurements (e.g., velocity encoded contrast MR and echo Doppler) in the 4D geometric model is generated. For example, measurements of a chamber's volume and a valve's opening area computed over a full cardiac cycle enable for the characterization of the hemodynamics. Blood quantity, pressure and velocity can be directly estimated, for each of the four chambers, from the fitted 4D personalized anatomical heart model. The integration of Doppler echocardiogram or velocity encoded contrast MR velocity measurements further enhances the robustness of the blood parameter computation. Referring to FIG. 2, at step 206, the patient-specific 4D mesh is generated and velocity encoded contrast MR is generated at the aortic and mitral valve.

Returning to FIG. 1, at step 108, a patient specific biomechanical model is generated based on Fluid Structure Interaction (FSI) simulations using the 4D computational model. A detailed simulation of the blood flow pattern of the patient, as well as the interaction of the blood with the anatomical structures of the heart, can be obtained by combining the above described measurements with established biomechanical and hemodynamics models, and finite element methods. For example, using FSI techniques the blood flow and tissue interaction can be simulated using the parameters measured in the computational model. This enables the computation of path, pressure, and velocity of the blood on a particle level with a desired granularity. If material properties are not measured in the computational model FSI can be specialized to computational fluid dynamics (CFD) in order to obtain full blood flow simulation using only the patient specific dynamic geometry, without simulating interaction of the blood and the tissue.

In order to derive patient-specific anatomic and hemodynamic features from the computational models and use them subsequently for the identification of relevant risk factors and disease-progression models, a comprehensive simulation approach can be utilized. In addition to generating hemodynamic attributes for the decision support framework, the computational model is used as a tool for non-invasive assessment of surgical procedures on specific patients and for analyzing the effect of surgery on key parameters like wall shear stress and displacement. This is achieved by appropriately modifying the patient-specific structure model (e.g., to reflect surgical changes) together with the boundary conditions, and then simulating the blood flow in the simulated post-operative heart and aorta. At the same time, operational models can also be used to simulate physical stress and exertion conditions, to analyze its effect on the key hemodynamic attributes, and to incorporate it into the risk progression model to generally reflect the activity of daily living.

FSI methods can be tailored to the particular heart parts, as some parts perform an active role (e.g., ventricle) or a mixed passive/active role (e.g., valves, arteries). Exemplary FSI methods for various heart parts are described below.

Aorta (or other blood vessels): FSI models that include both fluid and structure equations fully coupled together through a set of boundary conditions, such as equal displacement, equal traction, and no-slip condition. This allows advanced bio-mechanical measurements such as wall stress, shear stress, elasticity, and stiffness. The wall can be modeled as a three-layer structure with different mechanical properties for the intima, media, and adventitia layers. According to an advantageous implementation, the wall can be modeled as an anisotropic material for more realistic FSI simulations.

Heart Chambers: Hemodynamic model based on Navier-Stokes equations and rigid structure assumption driven by moving boundary conditions associated with i) heart walls contractions/displacement during both diastolic and systolic cycled and ii) dynamic blood flow velocity/pressure boundary conditions at the flow entry and exit points.

Figure 8:
FIG. 8 illustrates exemplary results of a CFD based FSI simulation for an aortic valve.

Heart Valves: Immersed Boundary Method treating structures as parts as fluid with forces added to modify the Navier-Stokes equations and no-slip boundary condition. FIG. 8 illustrates exemplary results of a CFD based FSI simulation for an aortic valve.

In the example of FIG. 2, at step 208, CFD-based FSI simulation is performed on the patient-specific computational models.

Returning to FIG. 1, at step 110, patient-specific clinical parameters are extracted based on the patient-specific model and the FSI simulations. In particular, phenotypic, anatomic and hemodynamic are derived from the patient-specific model and the simulations. The personalized models enable direct quantification of morphological, dynamical, and bio-mechanical characteristics including: dilation of the entire length of the thoracic aorta including the aortic annulus, and sino-tubular junction, aortic arch, proximal and distal descending aorta; chamber size and mass; vessel wall thickness; luminal dilation and aortic compliance and stiffness by calculation of relations between change in segmental aortic diameters or volumes and central blood pressure. CFD simulations on the patient-specific anatomic models generate hemodynamic parameters that characterize the complex flow fields including turbulence, jets, and recirculation. These simulations can further be used to derive the wall shear stress, blood velocity flow field, wall displacement, wall Von Mises stress (tensile), and turbulence intensity (vorticity). As illustrated in FIG. 2, at step 210, morphological and dynamic parameters of the heart and aorta are extracted, as well as hemodynamic parameters including wall shear stress, tensile stress, compliance and stiffness, turbulence intensity, aortic dilation, and aortic pressure. Additional patient information (e.g., clinical, history, and genetic information) can also be input and used as parameters.

At step 112, patient-specific disease progression and risk stratification is performed based on the patient-specific phenotypic, anatomic, and hemodynamic parameters derived from the patient-specific 4D model and the FSI simulations. The disease progression and risk stratification are performed using a trained decision-support model. To support decision-making, multi-level Markov Cycle tree models can be used for both disease progression and risk stratification as a function of time. Individual patients are characterized and stratified based on their patient-specific dynamic heart model. Markov models for decision analysis provide a rich framework for integrating available patient information, stimulating disease progression based on time-dependent patient risk, and providing statistics of expected outcomes based on alternatives. According to a possible implementation, the models can be studies under various conditions, such as normal operation, after simulated surgical intervention, and under simulated stress conditions.

This stratification is reflected by differences in transition rates among disease states, as well as transition rates from each disease state to critical states. It can be performed using methods of cluster analysis and automated subgroup discovery. Traditional statistical methods, such as multivariate regression and significance tests, can be combined with modern machine learning methods, such as Support Vector Machines, SCR's, Probabilistic Boosting Trees, and Bayesian Networks. Predictive models enable the identification of individual risk factors, as well as combinations of characteristics that together are most strongly associated with patient outcomes, even if individually they are not predicative. As illustrated in FIG. 2, at step 212, decision support is performed based on the extracted parameters using a disease progression model. The disease progression model can reflect unique genetic disease signatures, physical stress and exertion, and various possible surgical outcomes. Heart specific disease progression and risk stratification is described in greater detail below.

Disease Progression Modeling: Disease progression can be modeled in terms of the continuous evolution and temporal fluctuations of the anatomic, morphological, hemodynamic and phenotype parameters extracted at step 110. At a particular time (t), the condition of an individual patient can be characterized in terms of the instantaneous values of variables that will constitute the present state of an individual patient (x(t)). Each patient is represented as a distinct point in a state-space, a high-dimensional space spanned by the various attributes of the patients, which completely defines the state. The state vector contains both continuous and discrete state variables, some of which are inherently inter-related with one another due to the various biological, physical, and physiological constraints. These are observed, measured, extracted from imaging studies, or simulated under patient-specific framework, as described above.

Disease progression is manifested in the state dynamics, which represents continuous progression of the disease and discontinuous discrete events of intervention therapies. This is represented as follows: $\dot{x}(t)=\Phi^i(x(t), w(t))$, $i\in I=\{1, 2, \ldots N\}$, where $\Phi^i$ is the dynamics of the progression after the treatment i, trajectory x(t) defines the temporal progression of the disease, while the discrete state i(t) represents the broader changes that model the treatment or other sudden changes. i(t) can take on a finite set of values, determined by its dynamics $i(t)=\phi(i^-(t),x(t))$, and w(t) represents the external effects.

Figure 9:
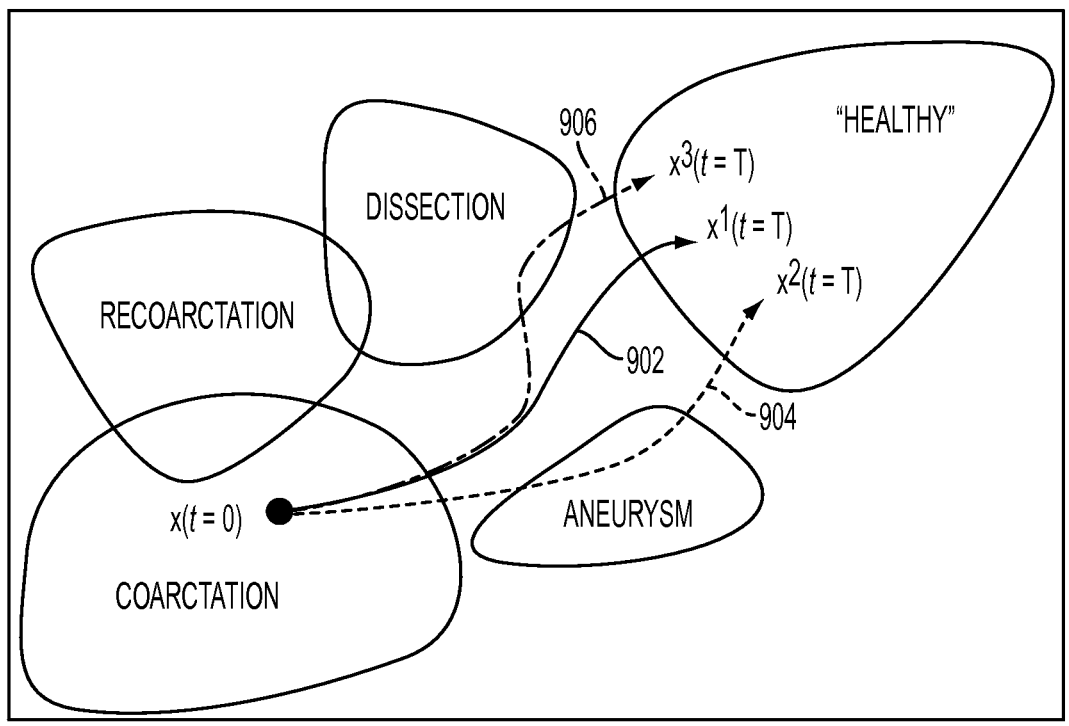
FIG. 9 illustrates disease progression trajectories for coarctation.

FIG. 9 illustrates disease progression trajectories for coarctation. As illustrated in FIG. 9, the trajectories 902, 904, and 906 represents disease trajectories under different interventions/treatments. As shown in FIG. 9, each trajectory 902, 904, and 906 begins in coarctation and ends with the patient being healthy. FIG. 9 also shows complications or dissection, aneurysm, and recoarctation that the trajectories 902, 904, and 906 can pass through. According to an embodiment of the present invention, in order to determine the progression trajectories, a non-linear similarity measure is learned and then used to distinguish specific patient groups. This is done by integrating measurements of morphology, dynamics, hemodynamics, material properties, phenotype and therapeutic procedures, obtained at multiple phases along the clinical workflow (i.e. pre-intervention and subsequent follow-ups). Hence, each patient profile is represented as a multi-dimensional vector of features. From the comprehensive set of quantities, we isolate individual patients in classes, specific to the clinical use cases for a particular cardiovascular disease. The probability that classifies patients in clinical relevant disease progression clusters is learned from equivalence constraints, able to capture statistics from heterogeneous input measurements. Non-linear regression is applied to estimate the probability, which models a similarity measure between a pair of two patient profiles. During clinical decision-making, the profile of the subject patient is compared to each individual in the training population, while the k-Nearest Neighbor algorithm applied on the similarity scores performs the classification.

Risk Stratification: Risk stratification involves characterizing the risk for intra- or post-procedural complications for individual patients. Our proposed methodology involves applying a non-linear similarity measure to distinguish between two classes: low-risk patients and high-risk patients. The classification is performed separately for each type of complication associated with the particular cardiovascular disease of interest (e.g. in case of coarctation, the three complications are dissection, aneurysm and recoarctation). To distinguish between low- and high profiles, we integrate the measurements obtained during the clinical evaluation at stage (morphology, dynamics, hemodynamics, phenotype and material properties). Additionally, the feature vector used for classification contains parameters of specific therapies to be applied (e.g. surgery, percutaneous implant etc). The similarity measure is learned from patients that are pre-classified in low or high risk, based on their follow-up studies.

Figure 10:
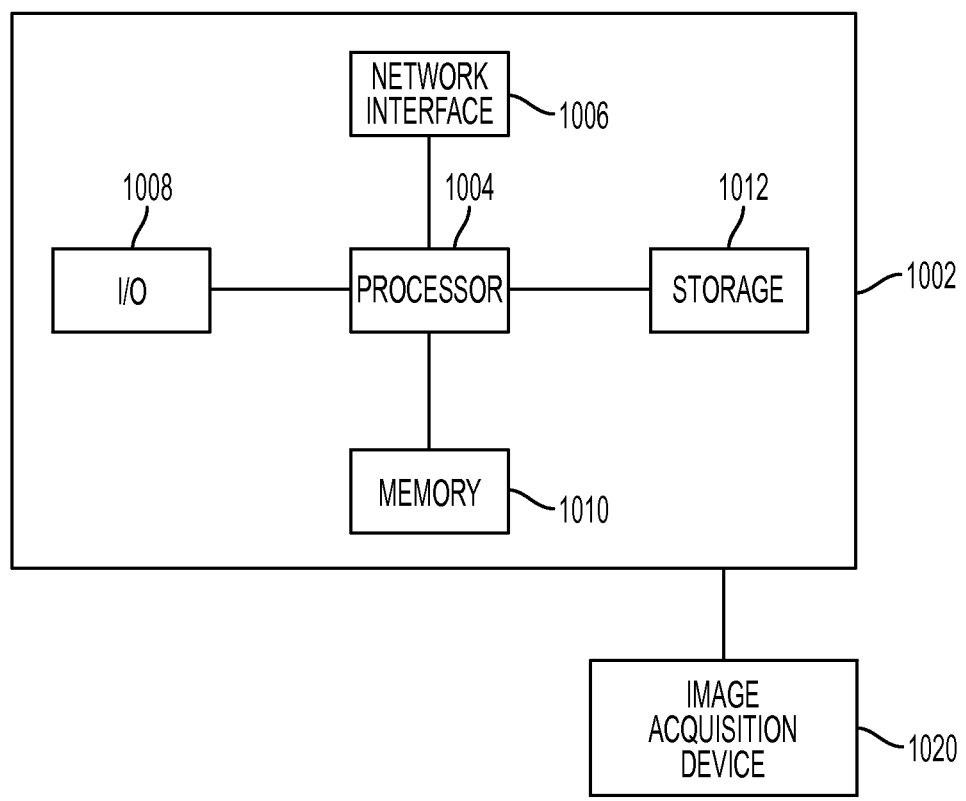
FIG. 10 is a high-level block diagram of a computer capable of implementing the present invention.

The above-described methods for generating a personalized anatomic model of the heart and performing disease progression modeling and risk stratification may be implemented on a computer using well-known computer processors, memory units, storage devices, computer software, and other components. A high-level block diagram of such a computer is illustrated in FIG. 10. Computer 1002 contains a processor 1004, which controls the overall operation of the computer 1002 by executing computer program instructions which define such operation. The computer program instructions may be stored in a storage device 1012 (e.g., magnetic disk) and loaded into memory 1010 when execution of the computer program instructions is desired. Thus, the steps of the method of FIGS. 1, 2, and 4 may be defined by the computer program instructions stored in the memory 1010 and/or storage 1012 and controlled by the processor 1004 executing the computer program instructions. At least one image acquisition device 1020, such as a CT scanning device, ultrasound device, MR scanning device, etc., can be connected to the computer 1002 to input the 3D volumes to the computer 1002. It is possible to implement the image acquisition device 1020 and the computer 1002 as one device. It is also possible that the image acquisition device 1020 and the computer 1002 communicate wirelessly through a network. The computer 1002 also includes one or more network interfaces 1006 for communicating with other devices via a network. The computer 1002 also includes other input/output devices 508 that enable user interaction with the computer 1002 (e.g., display, keyboard, mouse, speakers, buttons, etc.). Such input/output devices 1008 may be used in conjunction with a set of computer programs as an annotation tool to annotate volumes received from the image acquisition device 1020. One skilled in the art will recognize that an implementation of an actual computer could contain other components as well, and that FIG. 10 is a high level representation of some of the components of such a computer for illustrative purposes.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A method for multi-component heart modeling and cardiac disease decision support, comprising:
    receiving at least one sequence of volumetric cardiac imaging data of a patient generated using at least one medical imaging modality;
    generating a multi-component patient specific 4D geometric model of the heart and aorta estimated from the at least one sequence of volumetric cardiac imaging data of the patient by:
        estimating individual 4D models for a plurality of heart components in said at least one sequence of volumetric cardiac imaging data, and
        generating a patient specific 4D geometrical heart model by integrating the individual 4D models for each of said plurality of heart components;
    generating a patient specific 4D computational model based on one or more of personalized geometry, material properties, fluid boundary conditions, and flow velocity measurements in the 4D geometric model;
    generating a patient specific biomechanical model based on Fluid Structure Interaction (FSI) simulations using the 4D computational model;
    extracting patient specific clinical parameters based on the 4D geometric model and the FSI simulations; and
    performing disease progression modeling and risk stratification based on the patient specific clinical parameters.

2. The method of claim 1, further comprising:
    determining morphological and dynamic parameters for any of a plurality of heart components based on the 4D geometric heart model.

3. The method of claim 2, further comprising:
    determining at least one hemodynamic parameter based on the biomechanical model.

4. The method of claim 3, wherein said at least one hemodynamic parameter comprises at least one of wall shear stress, compliance and stiffness, turbulence intensity, dilation pressure, and full heart blood velocity patterns.

5. The method of claim 1, wherein said step of receiving at least one sequence of volumetric cardiac imaging data of the patient generated using at least one medical imaging modality comprises:
    receiving at least one of a 4D computed tomography (CT) image sequence and a 4D echocardiography image sequence, and a 4D magnetic resonance imaging (MRI) sequence.

6. The method of claim 1, wherein said step of estimating individual 4D models for a plurality of heart components in said at least one sequence of volumetric cardiac imaging data comprises:

estimating individual models of a left ventricle (LV) endocardium, LV epicardium, right ventricle (RV), left atrium (LA), right atrium (RA), mitral valve, aortic valve, aorta, and pulmonary trunk.

7. The method of claim 1, wherein said step of generating a patient specific 4D geometrical heart model by integrating the individual 4D models for each of said plurality of heart components comprises:
  establishing mesh point correspondence between connecting ones of the individual models.

8. The method of claim 1, wherein:
  said step of estimating individual 4D models for a plurality of heart components in said at least one sequence of volumetric cardiac imaging data comprises estimating an individual model for each of said plurality of heart components in each frame of the at least one sequence of volumetric cardiac imaging data; and
  said step of generating a patient specific 4D geometrical heart model by integrating the individual 4D models for each of said plurality of heart components comprises generating a patient specific geometrical heart model in each frame of the at least one sequence of volumetric cardiac imaging data.

9. The method of claim 1, wherein said sequence of volumetric cardiac imaging data is generated over at least one heart cycle.

10. The method of claim 1, wherein said step of performing disease progression modeling and risk stratification based on the patient specific clinical parameters comprises:
  generating at least one cardiac disease progression model based on the extracted clinical parameters using a multi-level Markov Cycle Tree model.

11. The method of claim 1, wherein said step of performing disease progression modeling and risk stratification based on the patient specific clinical parameters comprises:
  generating at least one cardiac disease progression model having a plurality of trajectories corresponding to a plurality of alternative treatments and one or more disease complications through which the trajectories pass.

12. The method of claim 1, wherein said step of performing disease progression modeling and risk stratification based on the patient specific clinical parameters comprises:
  classifying the patient as low-risk or high risk for each complication associated with one or more cardiac diseases.

13. An apparatus for multi-component heart modeling and cardiac disease decision support, comprising:
  means for generating a multi-component patient specific 4D geometric model of the heart and aorta estimated from a sequence of volumetric cardiac imaging data of a patient generated using at least one medical imaging modality comprising:
    means for estimating individual 4D models for a plurality of heart components in said at least one sequence of volumetric cardiac imaging data, and
    means for generating a patient specific 4D geometrical heart model by integrating the individual 4D models for each of said plurality of heart components;
  means for generating a patient specific 4D computational model based on one or more of personalized geometry, material properties, fluid boundary conditions, and flow velocity measurements in the 4D geometric model; and
  means for generating a patient specific biomechanical model based on Fluid Structure Interaction (FSI) simulations using the 4D computational model;
  means for extracting patient specific clinical parameters based on the 4D geometric model and the FSI simulations; and
  means for performing disease progression modeling and risk stratification based on the patient specific clinical parameters.

14. The apparatus of claim 13, wherein said means for performing disease progression modeling and risk stratification based on the patient specific clinical parameters comprises:
  means for generating at least one cardiac disease progression model based on the extracted clinical parameters using a multi-level Markov Cycle Tree model.

15. The apparatus of claim 13, wherein said means for performing disease progression modeling and risk stratification based on the patient specific clinical parameters comprises:
  means for generating at least one cardiac disease progression model having a plurality of trajectories corresponding to a plurality of alternative treatments and one or more disease complications through which the trajectories pass.

16. The apparatus of claim 13, wherein said means for performing disease progression modeling and risk stratification based on the patient specific clinical parameters comprises:
  means for classifying the patient as low-risk or high risk for each complication associated with one or more cardiac diseases.

17. A non-transitory computer readable medium encoded with computer executable instructions for multi-component heart modeling and cardiac disease decision support, the computer executable instructions defining steps comprising:
  receiving at least one sequence of volumetric cardiac imaging data of the patient generated using at least one medical imaging modality;
  generating a multi-component patient specific 4D geometric model of the heart and aorta estimated from the at least one sequence of volumetric cardiac imaging data of the patient generated using at least one medical imaging modality by:
    estimating individual 4D models for a plurality of heart components in said at least one sequence of volumetric cardiac imaging data, and
    generating a patient specific 4D geometrical heart model by integrating the individual 4D models for each of said plurality of heart components;
  generating a patient specific 4D computational model based on one or more of personalized geometry, material properties, fluid boundary conditions, and flow velocity measurements in the 4D geometric model;
  generating a patient specific biomechanical model based on Fluid Structure Interaction (FSI) simulations using the 4D computational model;
  extracting patient specific clinical parameters based on the 4D geometric model and the FSI simulations; and
  performing disease progression modeling and risk stratification based on the patient specific clinical parameters.

18. The computer readable medium of claim 17, wherein the computer executable instructions defining the step of performing disease progression modeling and risk stratification based on the patient specific clinical parameters comprise computer executable instructions defining the step of:
  generating at least one cardiac disease progression model based on the extracted clinical parameters using a multi-level Markov Cycle Tree model.

19. The computer readable medium of claim 17, wherein the computer executable instructions defining the step of performing disease progression modeling and risk stratification based on the patient specific clinical parameters comprise computer executable instructions defining the step of:

generating at least one cardiac disease progression model having a plurality of trajectories corresponding to a plurality of alternative treatments and one or more disease complications through which the trajectories pass.

20. The computer readable medium of claim 17, wherein the computer executable instructions defining the step of performing disease progression modeling and risk stratification based on the patient specific clinical parameters comprise computer executable instructions defining the step of:

classifying the patient as low-risk or high risk for each complication associated with one or more cardiac diseases.

* * * * *